(12) United States Patent
Harttig et al.

(10) Patent No.: US 8,570,519 B2
(45) Date of Patent: Oct. 29, 2013

(54) METHOD AND DEVICE FOR ANALYZING A BODY FLUID

(75) Inventors: Herbert Harttig, Neustadt (DE); Hans-Peter Haar, Wiesloch (DE); Gerhard Werner, Weinheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/466,834

(22) Filed: May 8, 2012

(65) Prior Publication Data

US 2012/0281219 A1 Nov. 8, 2012

Related U.S. Application Data

(63) Continuation of application No. PCT/EP2010/067758, filed on Nov. 18, 2010.

(30) Foreign Application Priority Data

Nov. 18, 2009 (EP) .................................. 09176330

(51) Int. Cl.
  *G01N 21/00* (2006.01)
(52) U.S. Cl.
  USPC ............................................. 356/436; 356/39
(58) Field of Classification Search
  USPC ............................................ 356/39, 432, 436
  See application file for complete search history.

(56) References Cited

U.S. PATENT DOCUMENTS

| | | | | |
|---|---|---|---|---|
| 4,552,458 A * | 11/1985 | Lowne | ........................ | 356/446 |
| 4,818,710 A * | 4/1989 | Sutherland et al. | ........... | 436/527 |
| 5,424,035 A * | 6/1995 | Hones et al. | .................. | 422/404 |
| 5,563,042 A * | 10/1996 | Phillips et al. | .................. | 435/14 |
| 5,728,352 A * | 3/1998 | Poto et al. | .................... | 422/82.05 |
| 5,770,454 A * | 6/1998 | Essenpreis et al. | ............ | 436/164 |
| 5,780,304 A * | 7/1998 | Matzinger et al. | ............. | 436/169 |
| 5,843,692 A * | 12/1998 | Phillips et al. | .................. | 435/14 |
| 5,995,236 A * | 11/1999 | Roth et al. | ..................... | 356/445 |
| 6,027,692 A * | 2/2000 | Galen et al. | .................... | 422/82.05 |
| 6,055,060 A * | 4/2000 | Bolduan et al. | ............... | 356/433 |
| 6,201,607 B1 * | 3/2001 | Roth et al. | ..................... | 356/445 |
| 6,562,625 B2 * | 5/2003 | Modzelewski et al. | ........ | 436/44 |
| 6,707,554 B1 * | 3/2004 | Miltner et al. | ................ | 356/433 |
| 7,154,592 B2 * | 12/2006 | Reynolds et al. | ............... | 356/39 |
| 7,283,242 B2 * | 10/2007 | Thornton | ...................... | 356/432 |
| 7,477,404 B2 | 1/2009 | Schulat et al. | | |
| 7,508,498 B2 * | 3/2009 | Huang et al. | .................... | 356/39 |
| 7,577,469 B1 * | 8/2009 | Aronowitz et al. | ........... | 600/310 |

(Continued)

FOREIGN PATENT DOCUMENTS

| | | |
|---|---|---|
| EP | 1275964 A1 | 1/2003 |
| EP | 1447658 A1 | 8/2004 |

(Continued)

*Primary Examiner* — Roy M Punnoose

(74) *Attorney, Agent, or Firm* — Harness, Dickey

(57) ABSTRACT

Methods and devices for analyzing body fluids, in particular for determining blood glucose. Body fluid is applied to a test element for single-use in a test device and the test element is optically coupled to a photometric measuring unit by means of an optical transmission system, wherein a time course of measuring values is recorded after the body fluid has been applied in order to detect a component of the body fluid on the test element. The transmission behavior of the optical transmission system may be controlled by recording measuring values at two different measurement wavelengths.

15 Claims, 2 Drawing Sheets

(56) References Cited

U.S. PATENT DOCUMENTS

| | | | |
|---|---|---|---|
| 7,633,621 B2* | 12/2009 | Thornton | 356/432 |
| 7,758,812 B2* | 7/2010 | Pachl et al. | 422/82.05 |
| 7,817,255 B2* | 10/2010 | Huang et al. | 356/39 |
| 8,068,217 B2* | 11/2011 | Huang et al. | 356/39 |
| 8,325,329 B2* | 12/2012 | Sekimoto | 356/39 |
| 2004/0157341 A1* | 8/2004 | Reynolds et al. | 436/169 |
| 2006/0051738 A1* | 3/2006 | Zweig | 435/4 |
| 2006/0166302 A1* | 7/2006 | Clarke et al. | 435/25 |
| 2008/0249435 A1* | 10/2008 | Haar et al. | 600/583 |
| 2009/0247841 A1 | 10/2009 | Werner et al. | |

FOREIGN PATENT DOCUMENTS

| | | |
|---|---|---|
| EP | 2248463 A1 | 11/2010 |
| WO | 2006019543 A2 | 2/2006 |
| WO | 2008145628 A1 | 12/2008 |

* cited by examiner

METHOD AND DEVICE FOR ANALYZING A BODY FLUID

CROSS-REFERENCE TO RELATED APPLICATIONS

This application is a continuation of International Patent Application No. PCT/EP2010/067758, filed Nov. 18, 2010, which claims the benefit and priority of European Patent Application No. 09176330.0, filed Nov. 18, 2009. The entire disclosures of the above applications are incorporated herein by reference.

BACKGROUND

The invention concerns a method for analyzing a body fluid, in particular for determining blood glucose in which body fluid is applied to a test element for single-use in a test device and the test element is optically coupled to a photometric measuring unit by means of an optical transmission system, wherein a time course of measuring values is recorded after the body fluid has been applied in order to detect a component of the body fluid on the test element. The invention additionally concerns a corresponding test system.

Known methods of this type that are used in practice for blood glucose determinations are based on test strips which are constructed as optical single-use sensors that react irreversibly. When processed in automatic test devices, these test strips should also enable a layman to carry out a measurement of blood glucose with sufficient accuracy as required to medically treat the various forms of diabetes. The quality of the measurement is of particular importance especially for diabetes type 1 and also type 2 if treated with insulin. The measuring procedure provides that after a blood sample has been applied to the test strip, the analyte concentration is determined by repeated photometric measurements. In this connection it is important that the disposable reagent carrier system is not moved during the entire scanning process, e.g. for 4 to 10 seconds, in order to not interfere with the measurement.

SUMMARY

Based on this, the object of the invention is to further improve the known methods and devices in the prior art and in particular to further improve the quality and accuracy of the measuring process with the aim of also limiting the complexity of the apparatus which should thus be suitable for a compact system outside a laboratory environment.

The present technology provides methods for analyzing a body fluid, in particular for determining blood glucose in which body fluid is applied to a test element for single-use in a test device and the test element is optically coupled to a photometric measuring unit by means of an optical transmission system, wherein a time course of measuring values (i.e., measurements) is recorded after the body fluid has been applied in order to detect a component of the body fluid on the test element, characterized in that the transmission behavior of the optical transmission system is monitored by recording measuring values, or measurements, at two different measurement wavelengths. Advantageous embodiments and further developments of the technology are described further herein.

The invention is based on the idea of obtaining additional information on the optical transmission path between the test disposable or test field and the reflection photometric measuring unit by means of a control measurement. Accordingly, the transmission behavior of the optical transmission system may be monitored by recording measuring values at two different measurement wavelengths. This enables one to monitor the state of the opto-mechanical coupling of the test element during the measuring process so that the validity and accuracy of the result can be better guaranteed. This advantageously enables the transmission behavior of an optical element integrated into the test element and, in particular, a light guide interface to be controlled. This is important especially also for those systems which use small amounts of sample and thus have relatively small dimensions in the area of the optical coupling as defined for example by the cross-section of light guides.

A difference in the transmission behavior of the optical transmission system is advantageously determined before and after applying the body fluid from a wavelength-dependent comparison of the measuring values, wherein a correction of the measuring values is carried out or the test result is rejected depending on the difference that is determined. In this process, an area wetted with body fluid is optically scanned at both measurement wavelengths after the sample of body fluid has been applied.

Another advantageous embodiment provides that the two measurement wavelengths are preferably not more than 50 nm away from each other in an absorption range of the test element that is sensitive or usable for the detection of the component. Excitation with such a narrow-band resolution can ensure that the transmission system essentially has the same optical properties at both measurement wavelengths.

It is, however, also conceivable that one measurement wavelength is in an absorption range of the test element that is usable for detecting the component and the other measurement wavelength serves as a matrix value and lies in a non-sensitive range outside thereof. The matrix value that is independent of the component or analyte enables optical interferences to be controlled without being influenced by the reaction system for the detection. On the other hand, it must be accepted that wavelength-dependent interfering effects may have an asymmetric effect in both measuring channels.

In order to obtain status information even before applying the sample, it is advantageous when a dry blank value is recorded by a measurement before the body fluid is applied to the test element as a measure for the initial transmission behavior of the optical transmission system.

Another improvement provides that a reference value for the transmission behavior of the optical transmission system is extrapolated from the time course of the measuring values at the two measurement wavelengths to a starting time after application of the body fluid. In this connection it is also advantageous to use the reference value as an offset correction of the measuring values when it is below a predetermined maximum tolerance deviation from the dry blank value.

In order to further increase the accuracy of the measurement, the measuring values recorded in a wavelength-dependent manner are correlated to one another preferably by calculating ratios so that interferences having an effect at both measurement wavelengths are eliminated.

In order to establish a direct relationship between both measuring channels, it is advantageous when the measurement values are recorded essentially simultaneously at the two measurement wavelengths at time intervals over a predetermined measurement period.

Also with regard to simplifying the apparatus, it is of particular advantage when the measurement wavelengths are defined by irradiating spectrally resolved excitation light preferably by means of light-emitting diodes. This eliminates the need for complicated filter systems in the optical path.

The use of the two wavelength measurements is particularly advantageous in a measuring environment in which at least a part of the optical transmission system is moved and/or deformed in the course of applying the body fluid to the test element.

With regard to a measurement system and in order to solve the aforementioned object it is proposed that the measuring unit is configured such that the transmission behavior of the optical transmission system is monitored by recording measuring values at two different measurement wavelengths. This likewise results in the advantages already described above in relation to the process.

With regard to the spatial separation between the site of measurement and sample application site, it is advantageous when the optical transmission system comprises at least one light guide integrated into the test device and/or into the test element.

The optical transmission system advantageously has an opto-mechanical coupling device to hold the test element on the instrument and at the same time to optically couple the test element. This is of particular advantage when the test element has an optical element that can be coupled by means of an optical interface and in particular an integrated light guide as a part of the optical transmission system.

A further improvement can be achieved by means of the fact that the measuring device has a light emitter emitting at two measurement wavelengths as a dual emitter. In this case it is advantageous when a beam combiner uniformly focuses the excitation light irradiated from the light emitter, preferably by two discrete light-emitting diodes. The light emitter preferably emits the two measurement wavelengths simultaneously. The optical transmission system is aligned onto a sample measurement zone which is uniformly wetted with body fluid after sample application so that a wet value can be detected at the two measurement wavelengths.

DRAWINGS

The invention is further elucidated in the following on the basis of the embodiment examples shown schematically in the drawings.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
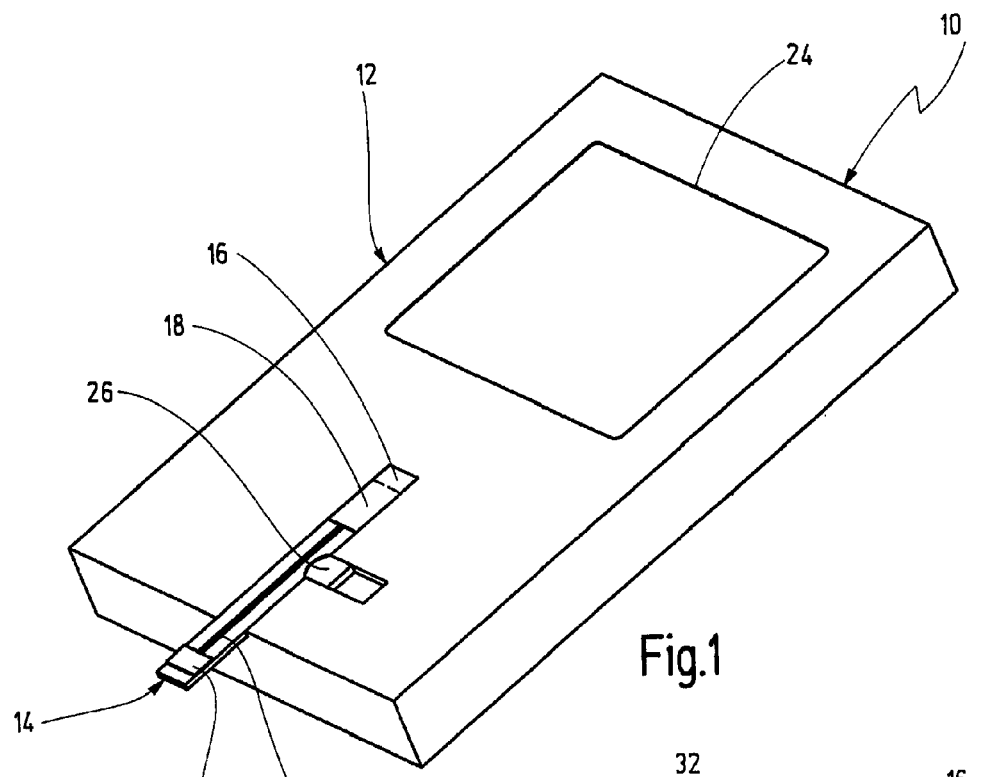
FIG. 1 shows a test system for blood glucose measurement using a hand-held device and a test strip inserted therein in a diagrammatic view.

The test system 10 shown in FIG. 1 comprises a portable test device 12 and test elements 14 that can be inserted therein each for a single-use test on a liquid sample and in particular for determining glucose in a blood sample. For this purpose the test device 12 has a photometric measuring unit 16 and an optical transmission system 18 for optically coupling the actively used test element 14, where the test element 14 is in the form of a test strip with a dry chemical test field 20 and a light guide arrangement 22 aligned thereon as part of the transmission system 18. In order to detect changes in the state of the optical coupling and the transmission behavior of the transmission system 18, the measuring unit 16 is designed to record measuring values in pairs at two different measurement wavelengths. The measurement result determined therefrom can for example be shown in the form of a digital concentration on the display 24.

The test element 14 that is in use can be docked mechanically onto the test device for example by means of a form-fitting coupling unit 26 while at the same time making the optical connection.

For a single-use test a user can apply a small amount of capillary blood to the test field 20 which is taken up into a dry chemical reagent layer and, depending on the glucose concentration, results in a photometrically measurable color change due to a known enzyme-selective reaction.

The test elements 14 are advantageously provided to the user from a magazine that is not shown and optionally disposed of using the magazine. It is basically possible to use a test tape for this purpose, where the test fields located thereon are positioned by tape transport. It is also conceivable to use integrated test elements which combine sample collection, application on the test field and optical coupling in an automated sequence of movements as described in European Patent Application Publication 2248463, List, published Nov. 10, 2010, to which reference is herewith made. In addition to blood glucose determination other analyses of target analytes in a body fluid such as tissue fluid also come into consideration.

A common feature of all these systems is that the boundary conditions for the measurement can be accidentally changed due to actuation by the instrument or interventions by the user during the preparation of the test element. For example the sample application can result in an unintentional deformation or displacement of the transmission system 18 by pressing a body part onto the test field 20. In addition the recording of the measuring values at the starting time of sample application is unreliable or inaccurate because the test field is not suddenly wetted in a homogeneous manner and the optical properties change. In order to alleviate the situation, it is possible to deploy the two wavelength measurement that is elucidated in more detail below to ensure the required accuracy of the measurement and robustness towards interferences in particular of the opto-mechanical connection with a low instrument complexity.

Figure 2:
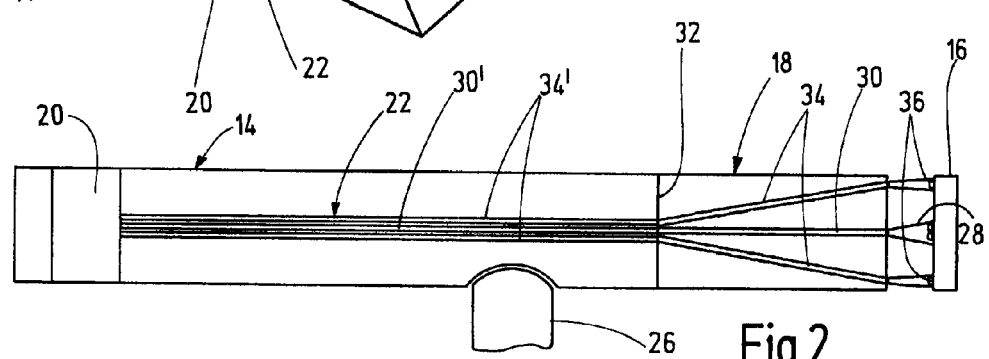
FIG. 2 shows a photometric measuring unit comprising an optical transmission system for a two wavelength measurement on the test strip in a top-view.

FIG. 2 illustrates the optical transmission path or optical path between the measuring unit 16 and the test field 20 of the docked test element 14. A light emitter 28 that emits as a dual emitter simultaneously at two different measurement wavelengths irradiates the excitation light into a central light guide 30 of the optical transmission system 18. The excitation light is transferred by means of the optical interface 32 into the middle light guide 30' of the light guide arrangement 22 integrated into the test element and reflects or scatters the excitation light upwards at its free end onto the rear side of the test field 20. The measurement light remitted from the test field 20 arrives at the light receiver 36 of the measuring unit via the outer light guides 34', 34, where the two receiving channels also enable monitoring of the wetting of the test field 20. The mechanical coupling unit 26 should also make or maintain a reliable optical connection in addition to correctly positioning the test element 14 at the interface 32.

Figure 3:
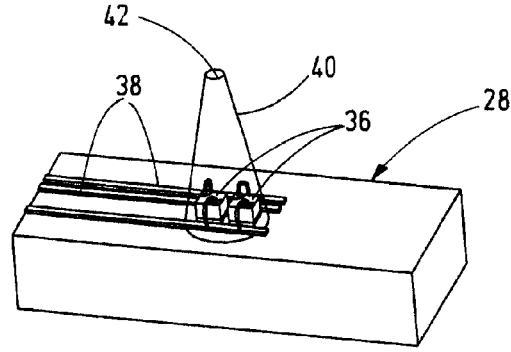
FIG. 3 shows a beam combiner for homogeneously feeding in the excitation light in a perspective view.

As shown in FIG. 3 the light emitter 28 can be in the form of two light-emitting diodes 36 which can be separately actuated by separate current paths 38. The light-emitting diodes 36 which emit almost monochromatically at different wavelengths to each other and thus in a spectrally resolved manner, are embedded in a reflector cone 40 made of a transparent plastic which thus acts as a beam combiner to focus the emitted light in a uniform manner and homogeneously mixed onto the exit cross-section 42.

Figure 4:
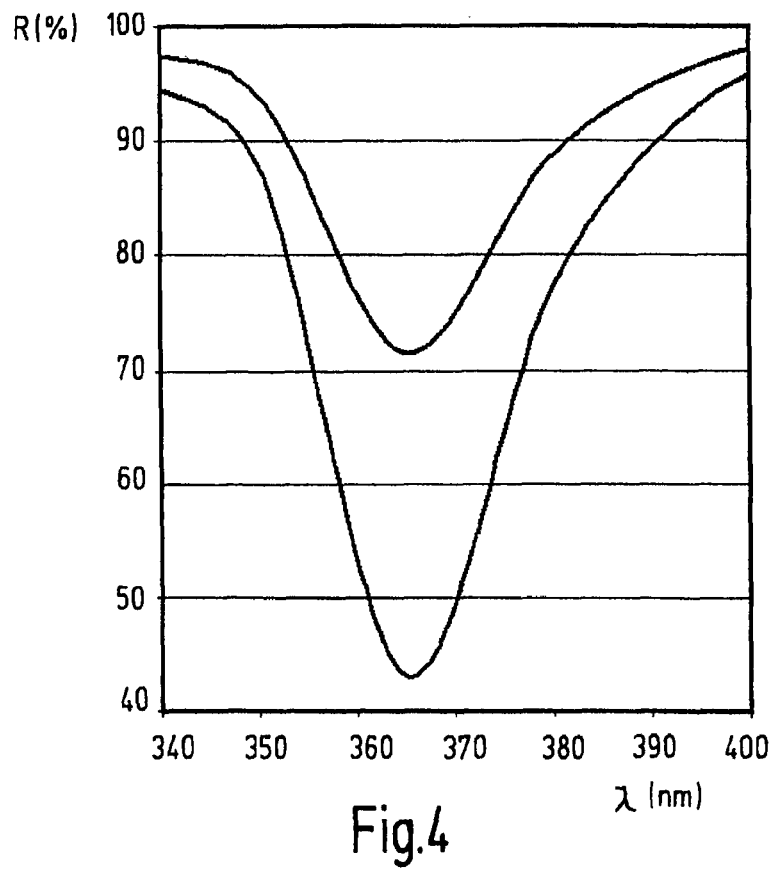
FIG. 4 shows a diagram of an absorption band of the test strip wetted with blood at various blood glucose concentrations.

FIG. 4 shows a graphic representation of absorption bands of the test field wetted with blood at two different glucose concentrations. It shows the diffuse reflection or remission R as a function of the wavelength λ at a given time after sample application. The upper curve shows the spectral curve for a glucose concentration of 100 mg/dl and the lower curve for a glucose concentration of 300 mg/dl. The two measurement wavelengths of 365 nm and 375 nm are within the usable absorption range for the detection of the analyte or for the glucose concentration determination. The measurement wavelengths are selected such that distinct remission differences in the absorption bands are observed whereas the transmission behavior of the optical transmission system remains substantially independent of the small difference in wavelength. However, it is basically also possible to select a control wavelength outside of the absorption band that is far removed from the measurement wavelength that is sensitive to glucose or the analyte within the absorption band.

Figure 5:
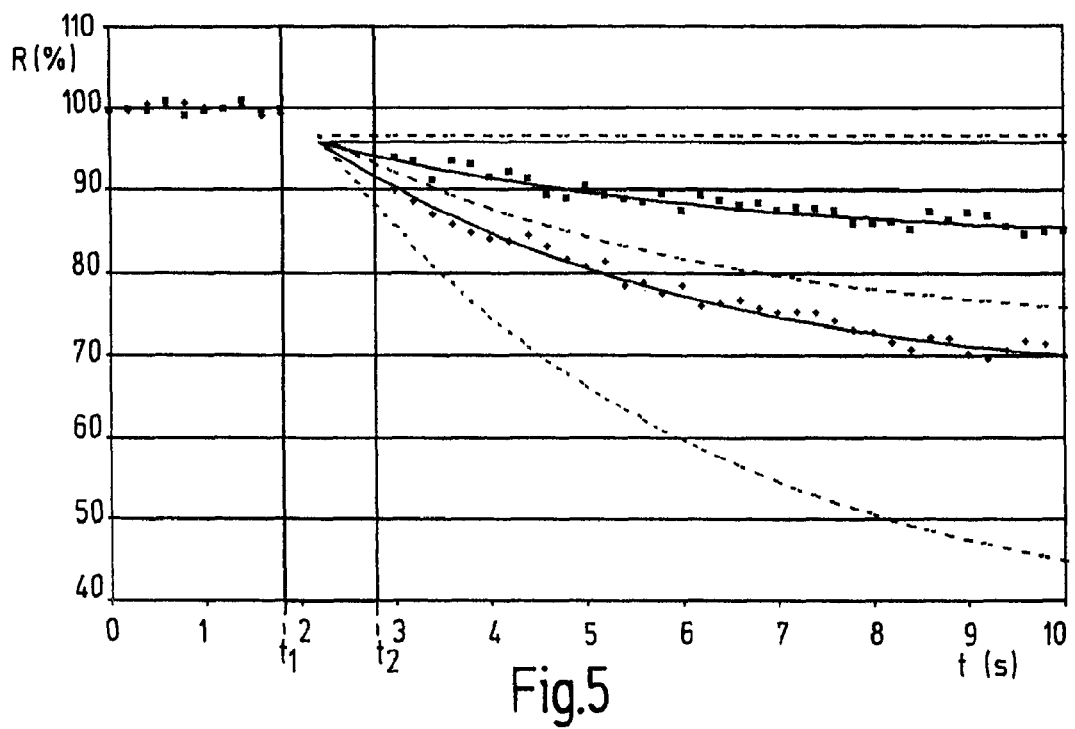
FIG. 5 shows a time course of remission measurement values at two blood glucose concentrations and in each case at two measurement wavelengths.

FIG. 5 shows time courses of intensity for two glucose concentrations obtained using a measuring system according to FIG. 2 and corresponding to the absorption spectrum of FIG. 4. The diagram shows the remission R normalized to 100% over the time t. The initially dry test field 20 was loaded with a blood sample at time point t1 and scanned at two different measurement wavelengths in pairs almost simultaneously at time intervals of 200 ms. Due to the already mentioned measuring problems due to an incomplete wetting and reflection changes, no valid measuring values can be obtained in the time range between t1 and t2 marked by the perpendicular lines. In the diagram the diamond symbols show measuring values at 365 nm and the square symbols show measurements at 375 nm for a glucose concentration of 100 mg/dl, whereas the continuous curves show corresponding fits to these values. For the sake of clarity, only the fitted exponential curves are shown by dashed lines for the second glucose concentration of 300 mg/dl.

The measurement sequence and the evaluation are further elucidated in the following on the basis of the diagram of FIG. 5. Firstly, before applying the blood sample a dry blank value is recorded or determined from the measuring values in the time range between 0 and t1 as a measure for the initial transmission behavior of the transmission system 18. If in this plausibility check the dry blank value deviates by more than 10% from a specified batch value, it is already recognized as a fault and the measuring process is aborted.

Then the sample is applied and the analyte-related scanning of the measuring values at the two measurement wavelengths is carried out until an end time of for example 10 s. As the diagram in FIG. 5 clearly shows a reference value for the transmission behavior of the optical transmission system can be extrapolated from the time course of the measuring values at the two measurement wavelengths to a starting time point after application of the body fluid. In this process curve fits and extrapolations are carried out by means of a microprocessor of the measuring unit 16 with preset functions. The reference value is determined by the intersection point of the two fit curves and is represented in the diagram by a horizontal line.

If the value falls below a specified maximum tolerance deviation of for example 5% from the dry blank value, the reference value can be used for an off-set correction of the measuring values. The intensity time course is then no longer based on the dry blank value but rather on the lowered reference value. In this connection it must be taken into consideration that a jump in the remission behavior occurs due to the dry-wet transition of the test field 20 which should be sufficiently constant.

If in contrast the difference between the dry blank value and the reference value is found to be too high, this implies a faulty transmission behavior of the transmission system 18. In this case the measurement is rejected and an error is displayed.

It is obvious from the intensity time course at only one wavelength that it is not possible to deduce the reference value in the time range between t1 and t2 because changes in the optical coupling and sample-related boundary conditions such as haematocrit value and temperature can lead to a change in the remission. This is also shown by the dashed intensity time course for the higher glucose concentration of 300 mg/dl in the diagram of FIG. 5 in which a higher reference value was recorded.

In order to take into account interferences that act equally at both measurement wavelengths, it is possible to mathematically eliminate an interfering factor C by forming a ratio of the measurement pairs $(R(365 \text{ nm})*C)/(R375 \text{ nm})*C)$ obtained in each case in one measurement interval.

It is basically possible to dispense with the dry blank value measurement and only to take the reference value into consideration for the correction of the measurements. It is also possible to provide analytical functions (e.g. exponential functions or polynomials) the parameters of which are fitted to the measuring values in order to thus calculate the glucose concentration. It is also possible to provide tables of values for various glucose values and to determine the best fitting of the measuring values. The tables and the parameter allocation can take place by means of batch-dependent coding. The temperature of the measurement system can be additionally recorded and incorporated into the evaluation. In any case the exact determination of the starting time point and the associated optical measuring values is important for an accurate determination of the glucose value.

It is also conceivable that one of the two measurement wavelengths is selected such that the control signals obtained at this wavelength react more sensitively to the transmission interferences than the actual measurement signal at the other wavelength. In doing so it is possible to optimize the transmission behavior of the optical transmission system for the measurement wavelength. It is also possible to utilize other signal properties and in particular polarization and/or an impulse shape of the signals that are coupled into and out of the transmission system, in addition to the wavelength-dependent status measurement.

What is claimed is:

1. A method for analyzing a body fluid, in particular for blood glucose determination, in which body fluid is applied to a test element for single-use in a test device and the test element is optically coupled to a photometric measuring unit by means of an optical transmission system, the method comprising:

recording a time course of measurements after the body fluid has been applied in order to detect a component of the body fluid on the test element, monitoring the transmission behavior of the optical transmission system by recording measurements at two different measurement wavelengths, and determining a difference in the transmission behavior of the optical transmission system before and after applying the body fluid from a wavelength-dependent comparison of the measurements.

2. The method according to claim 1, wherein a correction of the measurements is carried out or the test result is rejected depending on the difference that is determined.

3. The method according to claim 1, wherein the two measurement wavelengths are not more than 50 nm away from each other in an absorption range of the test element that is usable for the detection of the component.

4. The method according to claim 1, wherein one measurement wavelength is in an absorption range of the test element that is usable for detecting the component and the other measurement wavelength lies outside thereof.

5. The method according to claim 1, wherein a dry blank value is recorded by a measurement before the body fluid is applied to the test element as a measure for the initial transmission behavior of the optical transmission system.

6. The method according to claim 1, wherein a reference value for the transmission behavior of the optical transmission system is extrapolated from the time course of the measurements at the two measurement wavelengths to a starting time after application of the body fluid.

7. The method according to claim 6, wherein the reference value is used as an offset correction of the measurements when it is below a predetermined maximum tolerance deviation from the dry blank value.

8. The method according to claim 1, wherein the measurements recorded in a wavelength-dependent manner are correlated to one another by calculating ratios so that interferences having an effect at both measurement wavelengths are eliminated.

9. The method according to claim 1, wherein the measurement values are recorded essentially simultaneously at the two measurement wavelengths at time intervals over a predetermined measurement period.

10. The method according to claim 1, wherein the measurement wavelengths are defined by irradiating spectrally resolved excitation light by means of light-emitting diodes.

11. The method according to claim 1, wherein at least a part of the optical transmission system is moved and/or deformed in the course of applying the body fluid to the test element.

12. A device for analyzing a body fluid, in particular for blood glucose determination, comprising a portable test device having a photometric measuring unit and a test element coupled to the measuring unit by means of an optical transmission system, where body fluid is applied to the test element for a single-use test, the measuring unit is configured such that the transmission behavior of the optical transmission system is monitored by recording measurements at two different measurement wavelengths, and a difference in the transmission behavior of the optical transmission system is determined before and after applying the body fluid from a wavelength-dependent comparison of the measurements.

13. The device according to claim 12, wherein the optical transmission system comprises at least one light guide integrated into the test device and/or into the test element.

14. The device according to claim 12, wherein the optical transmission system has an opto-mechanical coupling device to hold the test element and at the same time to optically couple the test element.

15. The device according to claim 12, wherein the measuring unit has a light emitter emitting at two measurement wavelengths as a dual emitter, and that a beam combiner uniformly focuses the excitation light irradiated from the light emitter by two light-emitting diodes.

\* \* \* \* \*